(12) United States Patent
Peterson et al.

(10) Patent No.: US 10,173,957 B2
(45) Date of Patent: Jan. 8, 2019

(54) PROCESS FOR ACETIC ACID RECOVERY FROM AQUEOUS STREAMS

(71) Applicant: BP Corporation North America Inc., Naperville, IL (US)

(72) Inventors: David Peterson, Westmont, IL (US); Sameer Talreja, Plainfield, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/394,365

(22) Filed: Dec. 29, 2016

(65) Prior Publication Data

US 2017/0190650 A1    Jul. 6, 2017

Related U.S. Application Data

(60) Provisional application No. 62/273,780, filed on Dec. 31, 2015.

(51) Int. Cl.
| | | |
|---|---|---|
| *C07C 209/00* | (2006.01) | |
| *C07C 51/47* | (2006.01) | |
| *B01D 17/02* | (2006.01) | |
| *B01D 61/02* | (2006.01) | |
| *C02F 1/28* | (2006.01) | |
| *C02F 1/44* | (2006.01) | |
| *C07C 51/265* | (2006.01) | |
| *C02F 101/32* | (2006.01) | |

(52) U.S. Cl.
CPC .......... *C07C 51/47* (2013.01); *B01D 17/0202* (2013.01); *B01D 61/025* (2013.01); *C02F 1/281* (2013.01); *C02F 1/283* (2013.01); *C02F 1/286* (2013.01); *C02F 1/441* (2013.01); *C07C 51/265* (2013.01); *C02F 2101/32* (2013.01)

(58) Field of Classification Search
CPC ........................................................ C07C 51/47
USPC ........................................................ 562/414
See application file for complete search history.

(56) References Cited

U.S. PATENT DOCUMENTS

2008/0216649 A1* 9/2008 Huang ................ B01D 53/228
                                                                    95/50

FOREIGN PATENT DOCUMENTS

| EP | 1 541 217 | 6/2005 |
|----|-----------|--------|
| JP | 2002 326970 | 11/2002 |

OTHER PUBLICATIONS

H. Alper et al., Hydrocarbon Removal by Mycelx Filtration, Mycelx Technologies Corporation,www.mycelx.com, pp. 1-7.
H. Alper et al. Removal of Oils and Organic Compounds from Water and Air with Mycelx HRM (Hydrocarbon Removal Matrix) Technology, Presented in the Federal Facilities Environme.
T. Hodgkiess, et al. "Effect of Hydrocarbon Contaminants on the Performance of RO Membranes", Desalination 138 (2001) 283-289.

* cited by examiner

*Primary Examiner* — Deborah D Carr
(74) *Attorney, Agent, or Firm* — Robert N. Carpenter

(57) ABSTRACT

A process for removing acetic acid from an aqueous stream containing yellow oil. According to the process, yellow oil is removed from the aqueous stream prior to the removal of acetic acid by a reverse osmosis membrane.

16 Claims, 1 Drawing Sheet

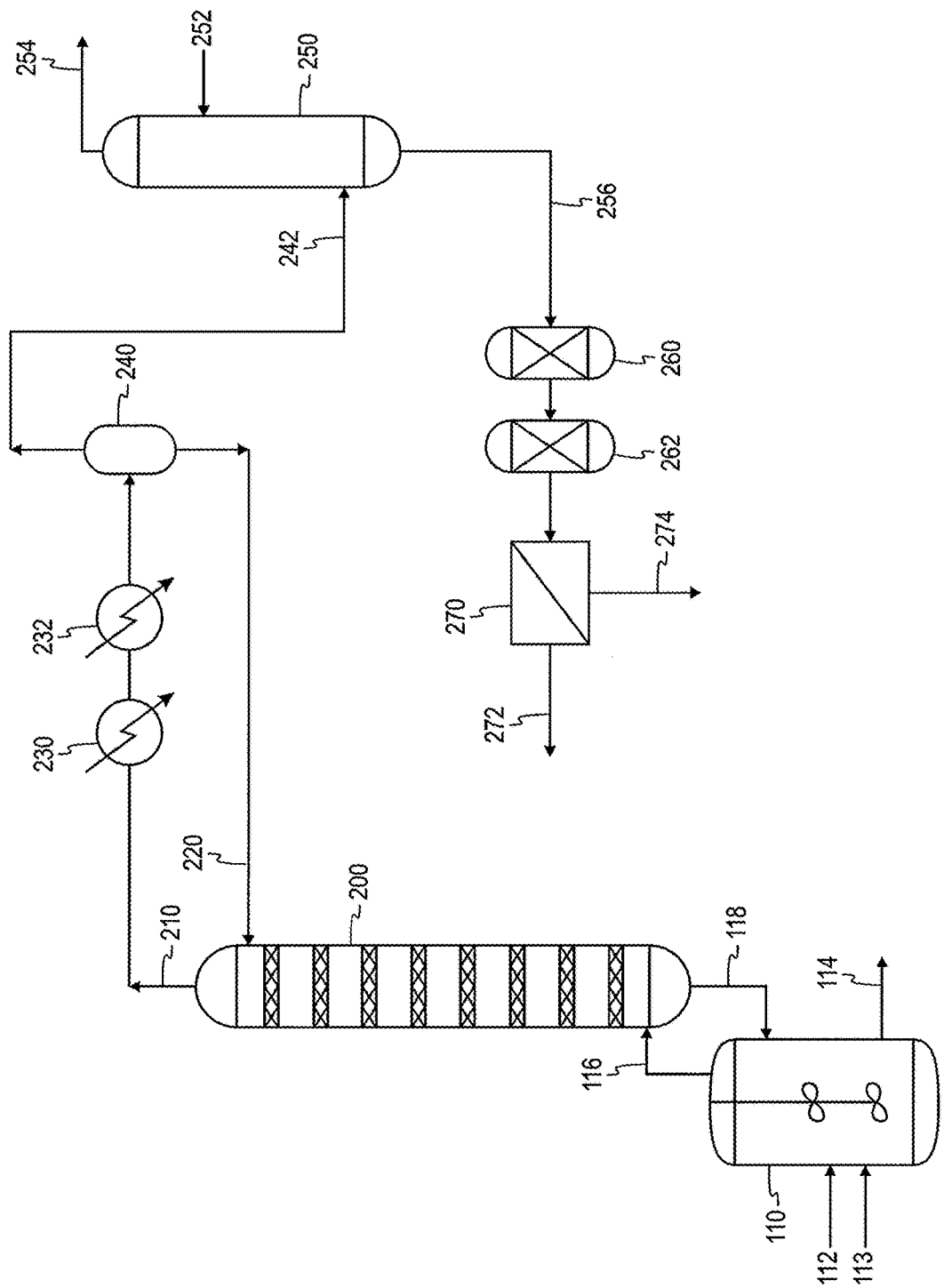

PROCESS FOR ACETIC ACID RECOVERY FROM AQUEOUS STREAMS

TECHNICAL FIELD

The present teachings relate generally to processes for the recovery of acetic acids from aqueous streams, and in particular, to improving processes for removing acetic acid utilizing membrane separation.

BACKGROUND

Membrane separation is an important unit operation in chemical processing. One known type of membrane separation utilizes reverse osmosis. In reverse osmosis, a semipermeable membrane operates as a molecular filter to separate a solution into a solute and solvent. With the solution in contact with the semipermeable membrane, an external pressure greater than the osmotic pressure of the solution is applied across the semipermeable membrane, causing the solvent to pass through, or permeate, through the membrane, while allowing the solute to remain behind.

One of the chemical processes utilizing this type of membrane separation is the manufacture of terephthalic acid. Terephthalic acid (TA) is used in the manufacture of polyesters. Polyesters in turn may be used to make fibers, films, containers, bottles, other packaging materials, molded articles, and the like.

In commercial practice, terephthalic acid has been made by liquid phase oxidation of paraxylene in an aqueous acetic acid solvent. Air or other sources of oxygen have been used as oxidants in the presence, for example, of a bromine-promoted catalyst that contains cobalt and manganese. The oxidation is exothermic and yields aromatic carboxylic acid together with by-products, including partial or intermediate oxidation products of paraxylene, such as paratoluic acid, and acetic acid reaction products (e.g., methanol, methyl acetate, and methyl bromide). Water is also generated as a by-product.

In a typical commercial process, an acetic acid-rich gaseous phase exits the reactor and enters a high pressure dehydration tower for separation of acetic acid and water. The acetic acid is recovered and returned to the oxidation reactor. A high pressure vapor phase containing small amounts of acetic acid and trace amounts of contaminants exits the tower. A portion of the high pressure vapor phase is used for energy recovery and another portion is condensed and used in other units of the process.

In order to reduce the need for fresh acetic acid solvent and for wastewater treatment, some prior processes have recovered acetic acid from the condensate. One method of recovering acetic acid from the condensate has been to use membrane separation, such as the use of a reverse osmosis membrane.

While the reverse osmosis membranes have been shown to be initially effective in recovering acetic acid, over time they have a tendency to exhibit a significant decrease in permeate flux and increase in solute passage. This decrease in performance leads to early replacement of the reverse membrane, adding a significant cost to the process.

There remains a need to efficiently and reliably recover acetic acid from an aqueous stream in chemical processes using membrane separation.

SUMMARY

The present invention provides an efficient and reliable method for recovering acetic acid from an aqueous stream. The method utilizes a membrane separation zone that retains its initial or nearly its initial performance characteristics over longer periods of time compared to the prior art.

In one aspect of the invention, a process for removing acetic acid from an aqueous stream is provided. The process includes removing oily contaminants from the aqueous stream to form an oil-lean effluent; and removing acetic acid from the oil-lean effluent by passing the effluent through a membrane separation zone.

According to another aspect of the invention, a process for producing terephthalic acid includes reacting a feed material comprising paraxylene with gaseous oxygen in a liquid phase oxidation reaction mixture comprising acetic acid solvent and water and in the presence of a catalyst composition comprising at least one heavy metal component in a reaction zone at temperature and pressure effective to maintain a liquid phase oxidation reaction mixture and form terephthalic acid, impurities comprising oxidation by-products, and a high pressure vapor phase comprising acetic acid, water and minor amounts of the paraxylene, terephthalic acid and by-products; separating the high pressure vapor phase to form an acetic acid-rich, water lean liquid and a high pressure gas comprising water vapor; condensing the high pressure gas to form an aqueous stream; removing oily contaminants from the aqueous stream to form an oil-lean effluent; removing acetic acid from the effluent by passing the effluent through a membrane separation zone.

Other aspects of the invention will become apparent to those skilled in the art in view of the description that follows.

BRIEF DESCRIPTION OF THE DRAWING

FIG. 1 is process flow diagram illustrating a process according to one embodiment of the invention.

DETAILED DESCRIPTION

By way of general introduction, a process for recovering acetic acid from an aqueous stream comprises removing oily contaminants from the aqueous stream to form an effluent having a reduced concentration of oily contaminants; and removing acetic acid from the effluent by passing the effluent through a membrane separation zone. By removing the oily contaminants upstream of the membrane separation zone, acetic acid recovery is increased and the fouling of the membrane is reduced, resulting in a longer lifespan for the membrane.

The membrane separation zone is designed to include one or more membranes capable of separating acetic acid from water. In some embodiments, the membranes are reverse osmosis membranes. Exemplary chemical processes utilizing reverse osmosis membranes are disclosed, for example, in Japanese Patent No. 4431812.

The oil absorbing materials of the present invention are those capable of removing the oily contaminants from the aqueous stream. In one embodiment, the oily absorbing material comprises activated charcoal. In another embodiment, the oil absorbing material comprises walnut shell. In another embodiment, the oil absorbing material comprises clay beds. In one embodiment, the oil absorbing material comprises a curable polymeric surfactant. One suitable curable polymeric surfactant is sold by MYCLEX Technologies Corporation of Gainesville Ga.

In some embodiments, two or more oil absorbing materials are used to remove the oily contaminants. In some embodiments, the oil absorbing materials are arranged in filter cartridges.

In one embodiment, the aqueous stream is passed through a filter to remove particulates prior to feeding the aqueous stream to the oil absorbing material.

The oily contaminants in the aqueous stream are hydrophobic materials of significant viscosity to have a tendency to clog the pores of the membranes. In some embodiments, the oily contaminants are oily or waxy hydrocarbons. In some embodiments, the oily contaminants are oily contaminants are oily aromatic hydrocarbons. In some embodiments, the oily contaminants are polycyclic aromatic hydrocarbons (PAHs), including PAHs with fused aromatic rings (poylnuclear aromatics) and PAHs without fused rings. Examples of PAHs that may be removed as oily contaminants include biphenyl, terphenyl, benzyl fluorine, and phenyl anthracene.

In some embodiments, the aqueous stream is a product stream or waste water stream resulting from prior chemical processing. In another embodiment, the aqueous stream comprises a least a portion of a condensate recovered from prior chemical processing. In one particular embodiment, the aqueous stream is a portion of a condensate recovered from a process for manufacturing terephthalic acid. Exemplary processes for the production of terephthalic acid and purified terephthalic acid are further described, for example, in U.S. Pat. Nos. 5,723,656, 6,137,001, 7,935,844, 7,935,845, and 8,173,834.

In one embodiment, a feed material comprising paraxylene with gaseous oxygen in a liquid phase oxidation reaction mixture comprising acetic acid solvent and water is reacted in a reaction zone in the presence of a catalyst composition comprising at least one heavy metal component in a reaction zone at temperature and pressure effective to maintain a liquid phase oxidation reaction mixture and form terephthalic acid. Impurities comprising oxidation by-products, and a high pressure vapor phase comprising acetic acid, water and minor amounts of the paraxylene, terephthalic acid and by-products are also formed. The high pressure vapor phase is separated to form an acetic acid-rich, water lean liquid and a high pressure gas comprising water vapor; and the high pressure gas to form an aqueous stream. Oily contaminants are removed from the aqueous stream to form an effluent with a reduced concentration of oily contaminants, and acetic acid from the effluent by passing the effluent through a membrane separation zone. The acetic acid may be recycled to reaction zone.

In some embodiments, trace amounts of various compounds are present in the aqueous stream. In one embodiment, the aqueous stream comprises terephthalic acid. In another embodiment, the aqueous stream comprises paraxylene. In another embodiment, the aqueous stream comprises methyl acetate. In another embodiment, the aqueous stream comprises methyl hydroxide.

FIG. 1 shows a process flow diagram for manufacturing aromatic carboxylic acids in accordance with one embodiment of the present invention. The process includes a reaction zone comprising an oxidation reactor 110 configured for liquid phase oxidation of feedstock. Representative aromatic feedstock materials suitable for use in the oxidation reactor 110 include but are not limited to aromatic compounds (e.g., hydrocarbons) substituted at one or more positions with at least one group that is oxidizable to a carboxylic acid group. In some embodiments, the substituted aromatic compound comprises a methyl-, ethyl-, and/or isopropyl-substituted aromatic hydrocarbon. In some embodiments, the substituted aromatic compound comprises an alkyl-substituted benzene, o-xylene, p-xylene, m-xylene, or the like, or combinations thereof.

Representative aromatic carboxylic acids include but are not limited to terephthalic acid, trimesic acid, trimellitic acid, phthalic acid, isophthalic acid, benzoic acid, naphthalene dicarboxylic acids, and the like, and combinations thereof. In some embodiments, the present teachings are directed to manufacture of pure forms of terephthalic acid including purified terephthalic acid (PTA) and so-called medium purity terephthalic acids.

A representative type of oxidation that may be conducted in the oxidation reactor 110 is a liquid phase oxidation that comprises contacting oxygen gas and a feed material comprising an aromatic hydrocarbon having substituents oxidizable to carboxylic acid groups in a liquid phase reaction mixture. In some embodiments, the liquid phase reaction mixture comprises a monocarboxylic acid solvent and water in the presence of a catalyst composition comprising at least one heavy metal component (e.g., Co, Mn, V, Mo, Cr, Fe, Ni, Zi, Ce, Hf, or the like, and combinations thereof) and a promoter (e.g., halogen compounds, etc.). In some embodiments, the oxidation is conducted at elevated temperature and pressure effective to maintain a liquid phase reaction mixture and form a high temperature, high-pressure vapor phase. In some embodiments, oxidation of the aromatic feed material in the liquid phase oxidation produces aromatic carboxylic acid as well as reaction by-products, such as partial or intermediate oxidation products of the aromatic feed material and/or solvent by-products. In some embodiments, the aromatic carboxylic acid comprises terephthalic acid, and the oxidizing comprises contacting para-xylene with gaseous oxygen in a liquid phase oxidation reaction mixture that comprises acetic acid, water, and a bromine-promoted catalyst composition. The liquid-phase oxidation and associated processes may be conducted as a batch process, a continuous process, or a semi-continuous process. The oxidation may be conducted in one or more reactors.

In a representative embodiment, such as may be implemented as shown in FIG. 1, liquid feed material comprising at least about 99 wt. % substituted aromatic hydrocarbon, aqueous acetic acid solution (e.g., containing about 70 to about 95 wt. % acetic acid), soluble compounds of cobalt and manganese (e.g., such as their respective acetates) as sources of catalyst metals, bromine (e.g., hydrogen bromide) as catalyst promoter, may be continuously charged to oxidation reaction vessel 110 through inlets, such as inlet 112. A source of gaseous oxygen, such as compressed air, is fed through inlet 113.

In some embodiments, vessel 110 is a pressure-rated, continuous-stirred tank reactor. In some embodiments, stirring may be provided by rotation of an agitator, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

In some embodiments, para-xylene is oxidized in reactor 110, predominantly to terephthalic acid. By-products that may form in addition to terephthalic acid include but are not limited to partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead gaseous stream that comprises vaporized acetic acid, water vapor, gaseous by-products from the oxidation reaction, carbon oxides, nitrogen from the air charged to the reaction, unreacted oxygen, and the like, and combinations thereof.

In some embodiments, liquid effluent comprising solid oxidation products slurried in the liquid phase reaction mixture is removed from reaction vessel 110 through slurry outlet 114 and directed downstream for further processing and purification, as described, for example, in U.S. Pat. Nos. 5,723,656, 6,137,001, 7,935,844, 7,935,845, and 8,173,834.

The process further includes an off-gas treatment zone configured to treat at least a portion of the gaseous stream formed by oxidization of the substituted aromatic compound. A gaseous stream may be removed from the reactor 110 through vent 116 and sent to the distillation column 200. The distillation column 200 is configured to separate water from the solvent monocarboxylic acid and return a solvent-rich liquid phase to the reactor in line 118. A distilled water-rich gaseous stream is removed from the separation zone in line 210. In some embodiments, the distilled gaseous stream comprises nitrogen, oxygen, water, acetic acid, carbon oxides, and methyl bromide. At least a portion of the water-rich gaseous stream 210 is condensed in one or more condensors 230, 232, and flashed in vessel 240. In some embodiments, at least a portion of the resulting condensate is refluxed to the column 200 through line 220. Another portion of condensate may be used in the processing and purification of the crude aromatic acid 114, as described, for example, in U.S. Pat. Nos. 5,723,656, 6,137,001, 7,935,844, 7,935,845, and 8,173,834.

Uncondensed gas is then directed in line 242 to a high pressure absorber 250 configured for removal of volatile components. The volatile components can be removed by contacting the vapor with a liquid stream 252. In one embodiment, the liquid stream comprises an acetic acid-rich stream. In other embodiments, a second liquid stream (not shown) comprises a water rich stream. In one embodiment, the resulting scrubbing liquors in line 256 are directed to one or more filters 260, 262 containing oil absorbing materials. One suitable filter contains curable polymeric surfactant and is sold by MYCLEX Technologies Corporation of Gainesville GA. The oil-lean effluent from the filters 260, 262 is directed to a membrane separation zone containing one or more membranes 270. One suitable membrane is a reverse osmosis membrane for separating the stream into an acetic acid rich stream 272 and a water-rich stream 274. The water-rich stream 274 may be sent to a waste water treatment facility or used in other parts of the process. The acetic acid-rich stream 272 may be re-used in other parts of the process, for example, may be used as make-up solvent on the reactor 110.

Scrubbed vapor effluent from the absorber 250 is directed through line 252 for further processing (not shown), such as removal of organic impurities by catalytic oxidation and/or recovery of energy through the expansion of the vapor, for example, as described in in U.S. Pat. Nos. 5,723,656, 6,137,001.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for recovering acetic acid from an aqueous stream, the process comprising:
    removing oily contaminants from the aqueous stream to form an effluent with a reduced concentration of oily contaminants; and
    removing acetic acid from the effluent by passing the effluent through a membrane separation zone.

2. The process of claim 1, wherein the membrane separation zone comprises at least one reverse osmosis membrane.

3. The process of claim 1, wherein the oily contaminants comprises polycyclic aromatic hydrocarbons and derivatives thereof.

4. The process of claim 1, wherein removing the oil contaminants comprises passing the aqueous stream through at least one oil absorbing material.

5. The process of claim 1, wherein removing the oily contaminants comprises passing the aqueous stream through at least two oil absorbing materials.

6. The process of claim 4, wherein the oil absorbing material comprises a curable polymeric surfactant.

7. The process of claim 4, wherein the oil absorbing material comprises activated charcoal.

8. The process of claim 4, wherein the oil absorbing material comprises walnut shells.

9. The process of claim 4, wherein the oil absorbing material comprises clay beds.

10. The process of claim 1, wherein removing the oily contaminants comprises removing at least 99 wt % of the oily contaminants in the aqueous stream.

11. The process of claim 1, the aqueous stream comprises terephthalic acid.

12. The process of claim 1, wherein the aqueous stream comprises paraxylene.

13. The process of claim 1, wherein the aqueous stream comprises methyl acetate.

14. The process of claim 1, wherein the aqueous stream comprises methyl hydroxide.

15. The process of claim 1, further comprising removing particulates from the water-containing stream prior to removing the oily contaminants.

16. The process of claim 1, further comprising:
    reacting a feed material comprising paraxylene with gaseous oxygen in a liquid phase oxidation reaction mixture comprising acetic acid solvent and water and in the presence of a catalyst composition comprising at least one heavy metal component in a reaction zone at temperature and pressure effective to maintain a liquid phase oxidation reaction mixture and form terephthalic acid, impurities comprising oxidation by-products, and a high pressure vapor phase comprising acetic acid, water and minor amounts of the paraxylene, terephthalic acid and by-products;
    separating the high pressure vapor phase to form an acetic acid-rich, water lean liquid and a high pressure gas comprising water vapor; and
    condensing the high pressure gas to form said aqueous stream.

* * * * *